US00PP22051P2

(12) United States Plant Patent
van Kleinwee

(10) Patent No.: US PP22,051 P2
(45) Date of Patent: Jul. 26, 2011

(54) *LOBELIA* PLANT NAMED 'LOBSTRAHOB'

(50) Latin Name: *Lobelia erinus*
Varietal Denomination: Lobstrahob

(75) Inventor: Theodorus Cornelis van Kleinwee, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/804,303

(22) Filed: Jul. 19, 2010

(51) Int. Cl.
*A01H 5/00* (2006.01)

(52) U.S. Cl. ..... Plt./451

(58) Field of Classification Search ..... Plt./451
See application file for complete search history.

*Primary Examiner* — Kent L Bell

(74) *Attorney, Agent, or Firm* — S. Matthew Edwards

(57) ABSTRACT

A new *Lobelia* plant named 'Lobstrahob' particularly distinguished by the large light violet-blue flowers, medium green foliage, vigorous and well branched habit, early flowering and improved heat tolerance.

1 Drawing Sheet

Latin name of the genus and species of the plant claimed: *Lobelia erinus.*

Varietal denomination: 'Lobstrahob'.

BACKGROUND OF THE NEW PLANT

The present invention comprises a new *Lobelia,* botanically known as *Lobelia erinus,* and hereinafter referred to by the variety name 'Lobstrahob'.

'Lobstrahob' is a product of a planned breeding program. The new cultivar has large light violet-blue flowers, medium green foliage, vigorous, mounding and semi-trailing and well branched habit with early flowering.

'Lobstrahob' originated from a hybridization made in July 2004 in a controlled breeding environment in Enkhuizen, Netherlands. The female parent was the unpatented, proprietary plant designated 'E1080-3' with light blue flowers, more vigor, later to flower, and less trailing habit.

The male parent of 'Lobstrahob' was an unpatented, proprietary plant designated as 'D0041-1' with light blue flowers, less vigor, smaller flower size, and less heat resistance. The resultant seed was sown in February 2005.

'Lobstrahob' was selected as one flowering plant within the progeny of the stated cross in May 2005 in a controlled environment in Enkhuizen, Netherlands.

The first act of asexual reproduction of 'Lobstrahob' was accomplished when vegetative cuttings were propagated from the initial selection in May 2005 in a controlled environment in Enkhuizen, Netherlands.

BRIEF SUMMARY OF INVENTION

Horticultural examination of plants grown from cuttings of the plant initiated in May 2005, and continuing thereafter, has demonstrated that the combination of characteristics as herein disclosed for 'Lobstrahob' are firmly fixed and are retained through successive generations of asexual reproduction.

'Lobstrahob' has not been observed under all possible environmental conditions. The phenotype may vary significantly with variations in environment such as temperature, light intensity and day length.

Plant Breeder's Rights for this cultivar were applied for in Canada on Feb. 9, 2010 (#10-6823) and in CVPO on Sep. 29, 2009 (#2009/1913). 'Lobstrahob' has not been made publicly available more than one year prior to the filing of this application.

The following traits have been repeatedly observed and are determined to be basic characteristics of the new variety. The combination of these characteristics distinguishes this *Lobelia* as a new and distinct variety.

BRIEF DESCRIPTION OF THE PHOTOGRAPHS

The accompanying photographic drawing shows typical flower and foliage characteristics of 'Lobstrahob' with colors being as true as possible with an illustration of this type. The photographic drawing shows a flowering potted plant of the new variety and a close-up of a flowers.

DETAILED BOTANICAL DESCRIPTION

The plant descriptions, measurements, and aforementioned photographs were taken in Gilroy, Calif. from plants growing in a greenhouse trial in April 2010. These plants were approximately 13-14 weeks of age.

Color references are made to The Royal Horticultural Society Colour Chart (R.H.S.) 2001.

TABLE 1

DIFFERENCES BETWEEN THE NEW VARIETY 'LOBSTRAHOB' AND A SIMILAR VARIETY

| | 'Lobstrahob' | 'Loboudtis' (U.S. Plant Pat. No. 15,526) |
|---|---|---|
| Flower size: | Larger | Smaller |
| Size of white eye in flower color: | Bigger | Smaller |
| Flower color: | Lighter violet-blue | Darker violet-blue |
| Foliage color: | Lighter | Darker |

Plant:

*Form, growth and habit.*—Vigorous growth habit, dense and freely branched with medium long internodes.

*Plant height.*—13-18 cm.
*Plant height (inflorescence included).*—22-27 cm.
*Plant width.*—About 30 cm.
*Garden performance and tolerance to weather.*—Good.
*Crop time to flowering.*—About 10 weeks.

Roots:
*Number of days to initiate roots and develop roots.*—21-24 days at about 22 degrees C.
*Type.*—Fine, fibrous, free branching.
*Color.*—RHS N155B but whiter.

Foliage:
*Arrangement.*—Alternate.
*Immature, leaf color, upper surface.*—Between RHS 137B and RHS 137C.
*Lower surface.*—Closest to RHS 147C.
*Mature, leaf color, upper surface.*—Between RHS 137B and RHS 137C.
*Lower surface.*—Closest to RHS 147C.
*Length.*—4.2-5.0 cm.
*Width.*—1.2-1.5 cm.
*Shape.*—Ovate.
*Base shape.*—Acuminate.
*Apex shape.*—Abruptly acute.
*Margin.*—Serrate.
*Texture, upper surface.*—Glabrous and slightly glossy.
*Lower surface.*—Glabrous and slightly glossy.
*Color of veins, upper surface.*—RHS 137A becoming indistinct.
*Color of veins, lower surface.*—RHS 137C.

Stem:
*Quantity of main branches per plant.*—10-15.
*Color of stem.*—RHS 146A.
*Length of stem.*—About 20-30 cm.
*Diameter.*—0.3 cm.
*Length of internodes.*—2-3 cm.
*Texture.*—Sparsely hirsute.

Inflorescence:
*Type.*—Raceme, terminal (at stem end), composed of single flowers in an alternate arrangement, with one flower per node, subtended by a narrow leaflet.
*Blooming habit.*—Continuous through the growing season.
*Quantity of inflorescences per plant.*—About 100.
*Lastingness of individual blooms on the plant.*—5-7 days depending on temperature.
*Fragrance.*—None.
*Color of peduncle.*—RHS 147B but a little darker.
*Length of peduncle.*—About 16 cm.
*Peduncle diameter.*—0.2-0.3 cm.
*Texture.*—Slightly hispid.
*Color of pedicels.*—RHS 147B but a little darker.
*Length of pedicels.*—2-2.7 cm.
*Diameter of pedicels.*—0.1 cm.
*Texture.*—Slightly hispid.

Bud (just when starting to show color):
*Color.*—RHS 155C overlaid with some RHS 198D.
*Length.*—1.5 cm.
*Width.*—0.6 cm.
*Shape.*—Oblong or tubular.

Flower:
*Corolla type.*—Single, zygomorphic; upper lip has two small lobes and lower lip has three larger and broader lobes; lobes are fused at the base.

Immature inflorescence:
*Flower diameter.*—About 1.5 cm.
*Flower color, upper surface.*—RHS 97A.
*Lower surface.*—RHS 97B.

Mature inflorescence:
*Depth of flower.*—2.0 cm.
*Diameter of flower.*—2.1-2.3 cm.
*Color upper petals, upper surface.*—RHS 97A.
*Lower surface.*—RHS 97B with a hint of RHS 97A.
*Upper petals, length (from the corolla opening).*—0.8 cm.
*Upper petals, width.*—0.3 cm.
*Color lower petals, upper surface.*—Between RHS 97B and RHS 97C with blotches and margins of RHS 97A; and white basally with spots of RHS 97A.
*Lower surface.*—RHS 97C with RHS 97B margins and white basally.
*Lower petals, length (from the corolla opening).*—1.2 cm.
*Lower petals, width.*—0.7-0.8 cm.
*Petal shape.*—Obovate.
*Apex shape.*—Praemorse.
*Base.*—Fused.
*Margin.*—Entire.
*Petal texture.*—Smooth, upper surface is slightly pubescent.

Corolla tube:
*Color, outside, upper side.*—RHS 97C overlaid with RHS 96D.
*Lower side.*—RHS 97C with a mottled overlay of a hint of RHS 97A.
*Inside.*—RHS N155A with RHS N89D basally.
*Tube length.*—1.1-1.2 cm.
*Tube width.*—0.4 cm.
*Texture, inside.*—Hirsute.
*Outside.*—Papillose.

Calyx:
*Quantity and form.*—5 sepals in a whorl, fused at the base and somewhat funnel shaped.
*Color, upper surface.*—RHS 147A but a little lighter.
*Lower surface.*—RHS 147A but a little lighter.
*Length of sepals.*—0.6-0.7 cm.
*Width of sepals.*—0.1 cm.
*Shape.*—Ligulate.
*Apex shape.*—Acute.
*Base.*—Fused.
*Margins.*—Entire.
*Texture, upper surface.*—Glossy and glabrous.
*Lower surface.*—Slightly hirsute basally.

Reproductive organs:
*Pistil.*—1.
*Length.*—0.7-0.8 cm.
*Style color.*—RHS 144A.
*Style length.*—0.6-0.7 cm.
*Stigma color.*—RHS N82D but lighter.
*Stamens.*—5.
*Color of filaments.*—RHS 97C overlaid with RHS 96D and white basally.
*Length filaments.*—0.5 cm.
*Anther color.*—RHS N187B.
*Anther length.*—0.2 cm.
*Color of pollen.*—RHS 4D.
*Pollen amount.*—Abundant.
*Fertility/seed set.*—Has not been observed on this hybrid.

Disease/pest resistance: Disease/pest resistance has not been observed on this hybrid.

What is claimed is:

1. A new and distinct variety of *Lobelia* plant named 'Lobstrahob' substantially as illustrated and described herein.

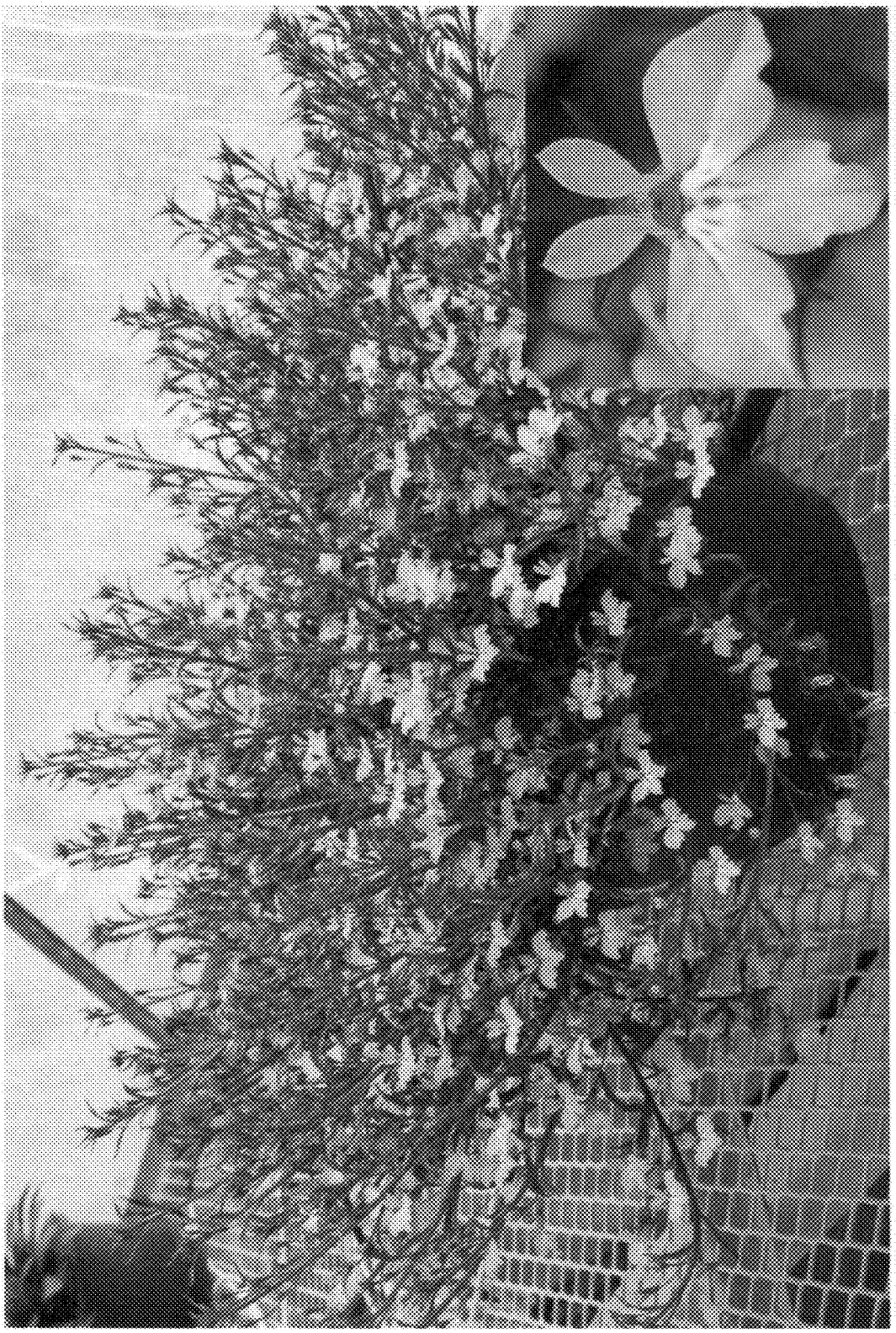

* * * * *